(12) United States Patent
Falkenstein

(10) Patent No.: US 9,797,710 B2
(45) Date of Patent: Oct. 24, 2017

(54) METHOD AND DEVICE FOR ESTABLISHING A GEOMETRY OF A CONTAINER FOR PACKAGING A FLOWABLE MEDIUM

(71) Applicant: Steinfurth Mess-Systeme GmbH, Essen (DE)

(72) Inventor: Martin Falkenstein, Bochum (DE)

(73) Assignee: Steinfurth Mess-Systeme GmbH, Essen (DE)

( * ) Notice: Subject to any disclaimer, the term of this patent is extended or adjusted under 35 U.S.C. 154(b) by 0 days.

(21) Appl. No.: 15/022,347

(22) PCT Filed: Sep. 9, 2014

(86) PCT No.: PCT/EP2014/069212
§ 371 (c)(1),
(2) Date: Mar. 16, 2016

(87) PCT Pub. No.: WO2015/036403
PCT Pub. Date: Mar. 19, 2015

(65) Prior Publication Data
US 2016/0282106 A1 Sep. 29, 2016

(30) Foreign Application Priority Data

Sep. 16, 2013 (DE) .................. 10 2013 110 202

(51) Int. Cl.
*G01J 5/02* (2006.01)
*G01B 11/06* (2006.01)
(Continued)

(52) U.S. Cl.
CPC .......... *G01B 11/0691* (2013.01); *G01B 11/02* (2013.01); *G01B 11/04* (2013.01);
(Continued)

(58) Field of Classification Search
CPC .................................................. G01B 11/105
See application file for complete search history.

(56) References Cited

U.S. PATENT DOCUMENTS

| 4,170,417 A | 10/1979 | Tourres |
| 4,751,386 A | 6/1988 | Gardner |

(Continued)

FOREIGN PATENT DOCUMENTS

| CH | 645462 | 3/1980 |
| EP | 698776 A2 * | 2/1996 |
| WO | WO 2015/036403 | 3/2015 |

OTHER PUBLICATIONS

International Search Report and the Written Opinion dated Nov. 14, 2014 From the International Searching Authority Re. Application No. PCT/EP2014/069212 and Its Translation of Search Report in English.

*Primary Examiner* — Kiho Kim

(57) ABSTRACT

The present invention relates to a device and a method for establishing a geometry of a container for packaging a flowable medium, wherein a radiation apparatus for generating and emitting at least electromagnetic radiation from a radiation source of the radiation apparatus to a radiation sink of the radiation apparatus along a detection region is activated in order subsequently to rotate and/or swivel the container about an axis of rotation by means of a movement apparatus, wherein, at least from time to time during a rotational movement of the container, at least one container region is moved through at least one portion of the detection region. Then, a detection apparatus is used to detect a passage time of the container region through the detection region, which passage time is evaluated by means of an evaluation apparatus for establishing an external geometry of the container.

14 Claims, 4 Drawing Sheets

(51) Int. Cl.
*G01B 11/02* (2006.01)
*G01B 11/04* (2006.01)
*G01B 11/10* (2006.01)
*G01B 11/24* (2006.01)
*G01J 5/10* (2006.01)
*G01N 21/47* (2006.01)
*G01N 21/55* (2014.01)
*G01N 21/59* (2006.01)

(52) U.S. Cl.
CPC .............. *G01B 11/10* (2013.01); *G01B 11/24* (2013.01); *G01J 5/10* (2013.01); *G01N 21/4738* (2013.01); *G01N 21/55* (2013.01); *G01N 21/59* (2013.01); *G01N 2201/06113* (2013.01)

(56) References Cited

U.S. PATENT DOCUMENTS

| | | | |
|---|---|---|---|
| 5,311,291 | A | 5/1994 | Cholet |
| 6,549,292 | B1 | 4/2003 | Schmidt et al. |
| 2008/0291438 | A1* | 11/2008 | Akkerman ............ B07C 5/3404 356/240.1 |

* cited by examiner

METHOD AND DEVICE FOR ESTABLISHING A GEOMETRY OF A CONTAINER FOR PACKAGING A FLOWABLE MEDIUM

RELATED APPLICATIONS

This application is a National Phase of PCT Patent Application No. PCT/EP2014/069212 having International filing date of Sep. 9, 2014, which claims the benefit of priority of German Patent Application No. 102013110202.6 filed on Sep. 16, 2013. The contents of the above applications are all incorporated by reference as if fully set forth herein in their entirety.

FIELD AND BACKGROUND OF THE INVENTION

The present invention relates to a method and a device for establishing a geometry of a container for packaging in particular a flowable medium.

Systems for establishing a surface or even the contour of objects are principally known. For example, there are tactile sensors which establish individual surface points of an object by mechanical scanning. Furthermore, it is known, for example, to use camera systems in particular for establishing an external contour of an object. Here, optically detectable two- or three-dimensional measuring points are detected by means of the camera system and transformed in such a manner that the system generates a corresponding image and consequently a two- or three-dimensional contour of the scanned object. For example, it is also possible that a light source for generating a light pattern on a surface of the object to be measured serves as a scanning device, wherein said light pattern is reflected by the surface and detected by a camera of the system. Such systems primarily serve for measuring an external contour of an object having a primarily radiation-reflecting surface. If the light radiation would be largely absorbed by the material of the object to be measured, this would result in an inaccurate or incorrect establishment of the external contour. In the worst case, measuring and establishing the external contour would not be possible at all. For example, measuring or establishing the external contour of an object, in addition to monitoring the production process of the object itself, can also serve for enabling the possibility to set up a subsequent machining process for machining the object in consideration of the contour and configuration of the object.

However, not only the external contour, but also the configuration of the inner contour and/or the dimensions of the wall thickness, in particular of a container such as, for example, a bottle or a food packaging, are values which are to be considered in the production process of the container itself or the bottling or filling process of the container, or in further tests such as, e.g., durability tests. Specifically in the case of durability tests, it is a disadvantage that the container in which the particularly liquid medium is disposed, for example, in the form of food or a beverage, often has to be opened or destroyed for the test. Non-destructive testing normally is performed using optical sensors. In particular for establishing the wall thickness and/or the external contour, it is basically known to use light and camera systems which are arranged along a production path for producing or treating containers in order to scan and measure different regions of the container in a time-consuming and cost-intensive manner so as to be able to establish individual values with regard to the geometry of the container. Accordingly, measuring a container is not only time-consuming, but also cost-intensive and prone to error due to the use of additional measuring apparatuses.

SUMMARY OF THE INVENTION

It is therefore an object of the present invention to eliminate the above-described disadvantages at least partially. In particular, it is an object of the present invention to provide a device and a method for establishing a geometry of a container which serves in particular as packaging of a flowable medium, and by means of which device and method, in addition to performing further functions, at least an external contour can also be established primarily in a simple and cost-effective manner. In doing so, already existing sensors are to be used.

The above object is achieved by a method for establishing a geometry of a container for packaging in particular a flowable medium having the features of claim 1, and by a device for establishing a geometry of a container for packaging in particular a flowable medium having the features according to claim 7. Further features and details of the invention arise from the sub-claims, the description and the drawings. Features and details described in connection with the method according to the invention apply of course also in connection with the device according to the invention and vice versa, so that always mutual reference is made or can be made with respect to the disclosure of the individual inventive aspects. Moreover, the method of the invention can be carried out on the device according to the invention.

The following text only writes about a flowable medium in the container, which is to be understood as any form of food, including solid, granular or viscous food or the like. However, the term "flowable medium" is in particular to be understood as any kind of beverages. The term "container" can preferably be a bottle made of glass or plastics, in particular PET bottles (PET—polyethylene terephthalate). Plastic bottles can be produced in an exact geometry; however, they are not necessarily pressure- and/or gas-tight over a longer period of time so that, e.g., $CO_2$ can escape from the beverages.

The method according to the invention for establishing a geometry of a container for packaging a flowable medium has at least the following steps:

activating a radiation apparatus for generating and emitting at least electromagnetic radiation from a radiation source of the radiation apparatus along a detection region to a radiation sink of the radiation apparatus, rotating and/or swiveling the container about an axis of rotation by means of a movement apparatus, wherein at least from time to time during a rotational movement of the container, at least one container region is moved through at least one portion of the detection region, detecting a passage time of the container region through the detection region by means of a detection apparatus, and establishing an external geometry at least from the passage time by means of an evaluation apparatus.

By means of the method according to the invention it is therefore conceivable to establish or detect an external contour or an external geometry of a container. The container itself can comprise, at least in some portions, a plastic material such as polyethylene, polypropylene, polyvinylchloride, acrylic glass or a glass material such as silicone dioxide or natural amber. Advantageously, the container serves for packaging a flowable and primarily liquid medium such as, for example, a beverage or drinkable food and for protecting it against quality damaging-influences.

However, it is also conceivable that the container serves for packaging products that otherwise need to be rendered nonperishable, such as frozen food, sausage products etc. Accordingly, it is possible that the container is a bottle or has a bottle-like configuration, wherein the container therefore has a container bottom and a mouth region including a neck region, for example. The neck region can have a smaller external container diameter than, for example, a region of the container bottom. During a preceding filling process, for example, the flowable medium can be introduced into the container via the mouth region, which advantageously has an opening. Furthermore, the container is preferably closed by means of a closure element attached on the opening in such a manner that neither the flowable medium nor gaseous medium, such as air, possibly contained in the container can escape from the container. Advantageously, a radiation apparatus including a radiation source and a radiation sink is activated in such a manner that the radiation source emits electromagnetic radiation and in particular electromagnetic waves such as, for example, infrared radiation, preferably towards the radiation sink. In doing so, the electromagnetic radiation passes through a region or space, hereinafter designated as detection region or detection space, which extends in particular three-dimensionally primarily between the radiation source and the radiation sink. However, it is also conceivable that the radiation sink on the device is not arranged opposite to the radiation source, but is arranged on the device on the same side as the radiation source so that the detection region extends starting from the radiation source and thus also starting from the radiation sink up to a reflection element which is primarily arranged on the device opposite to the radiation source and accordingly also to the radiation sink in the horizontal direction. In this case it is also possible that the radiation source is substantially the radiation sink. Thus, the radiation is emitted from the radiation source through the detection region up to the radiation sink, and from there reflected back through the detection region up to the radiation sink. Accordingly, it is conceivable here that the radiation apparatus also comprises the reflection element, in addition to the radiation sink and the radiation source. Furthermore, it is possible that the radiation source also emits a multiplicity of electromagnetic radiations substantially passing through (at one height) at least in some portions so that the individual beams, which, for example, pass through the detection region as linear beams, pass through the detection region in the form of a line radiation having a multiplicity of beams. Therefore, advantageously two or more beams are emitted over the height Hx from the radiation source, which can also have two and more radiation source units for emitting in each case a radiation or wave. When establishing the geometry of the container or in order to be able to establish this geometry of the container, the container is moved at least with one container region and primarily with a neck region or a mouth region at least from time to time during the establishing process or the measuring process through at least one region or portion of the detection region. For example, in the process of this, the container can be moved or swiveled or tilted about a center of rotation or an axis of rotation so that the container, at least temporarily, is moved from at least one horizontal position, in which the longitudinal axis extends substantially horizontally (parallel to the horizon), into a vertical position, in which the longitudinal axis of the container extends substantially vertical (perpendicular to the horizon). Advantageously, the container is moved or rotated or tilted until the at least one region and, in particular, the neck region of the container has passed completely through the detection region and has exited this region again. Ideally, this movement of the container through the detection region is performed at a defined and, in particular, constant speed v, which is known. The time $\Delta t$ or the points in time $T1$ and $T2$ from entering of the region of the container into the detection region until exiting of this region from the detection region is measured by means of a detection apparatus. This means that as soon as the radiation emitted from the radiation source is interrupted in such a manner that the radiation sink receives a changed and, in particular, a reduced radiation or receives a changed and, in particular, reduced radiation signal S due to, for example, the refraction and/or absorption of at least a part of the radiation or the beam on or by the wall or walls of the container, the detection apparatus detects entering of the at least one region of the container into the detection region. Accordingly, the detection apparatus can identify or detect exiting of the region of the container, for example, as soon as the radiation sink receives again the original intensity of the radiation which was present before entering of the container into the detection region. During the movement of the container, advantageously, not only measuring a geometry of the container takes place, but at the same time, at least temporarily, mixing of the media inside the container takes place as well. Thus, the flowable medium is mixed, for example, with a gaseous medium until advantageously a state of phase equilibrium between both media occurs so that, consequently, both media have the same pressure, in particular the same absolute pressure, and the same temperature. In particular in the case of carbon-dioxide-containing beverages it is required that the beverage has a predefined carbon dioxide concentration which is required for a certain quality and shelf life of the beverage. Thus, when bottling carbon-dioxide-containing beverages, it is required to check, in particular by means of sampling procedures, if the filled containers or bottles of a production batch contain a liquid or flowable medium which has a sufficient carbon dioxide concentration. For this purpose, in particular a region of a closure element can be pierced by means of a tapping mandrel, for example as part of a destructive testing method, in order to bring measuring elements such as a temperature sensor and/or a pressure sensor in fluid communication with the liquid and/or gaseous medium such as the carbon dioxide which escapes from the liquid medium. In order to be able to obtain measurement results that can be evaluated, it is required, inter alia, to generate a phase equilibrium between the media within the container. This can be enabled by mixing the existing media and/or temperature-controlling the media and/or releasing the gaseous medium from the liquid medium. If, for example, a gaseous medium is to be released from the liquid medium, the container is advantageously agitated or rotated or moved on a movement path, whereby a mixing of the media can take place. Such an intentionally caused release of gaseous medium from the liquid medium is also understood as sample preparation. Therefore, establishing the geometry of the container is advantageously carried out at least temporarily at the same time as the sample preparation, wherein advantageously no additional apparatus is required, whereby space can be saved, for example, in a test laboratory or even in the production line. In addition, the costs for testing and/or production are reduced due to a shortened test duration.

It is conceivable within the context of the invention that in addition to the external geometry or the external contour of the container, the internal geometry of the container is also established. Here, the internal geometry of the container is advantageously established or calculated from a value of the external geometry and a value of a wall thickness of the container. The device used for this purpose can be, for example, a calculation apparatus, wherein it is also conceivable that the previously mentioned detection apparatus performs the establishment of the internal geometry. Values of the wall thickness, in particular a wall thickness in the mouth region and/or neck region and/or head region or head space of the container can be stored or recorded for different containers and accordingly for different external geometries in a data base within a storage apparatus, for example. Thus, it is conceivable that the detection region detects a passage time of the container portion through the detection region, thereby establishes an external geometry, transmits these values, for example, to a calculation apparatus which, in turn, reads from the data base the values correlating to the established values for a wall thickness of the container and therefore establishes therewith the internal contour of the container.

Furthermore, it is conceivable that at least one value of the wall thickness of the container and preferably also a multiplicity of values for the wall thickness, in particular in different regions, in particular at different heights of the container, are/is established by means of the radiation apparatus and/or by means of a second radiation apparatus. To this end, it is conceivable that the first radiation apparatus, which is primarily also used for establishing the external contour or external geometry of the container, is swiveled or positioned, for example, in such a manner that the radiation is guided through only one wall of the container (without being deflected through the interior) before the radiation is absorbed by the radiation sink. Due to radiation intensity and/or radiation scattering impinging on the radiation sink it would therefore now be possible to establish the wall thickness at least in one region of the container. When this beam now also impinges on the interior of the container, a change in radiation intensity and/or scattering takes place again. Since it is also possible to measure the time $\Delta t$ or, respectively, the times T1 and T2 from entering of the region of the container wall into the detection region to exiting of the region from the detection region, the wall thickness at the point of the detection region can be established from the time information and the movement speed v of the container. The exit of the region of the container interior or, respectively, of the container wall from the detection region is also to be established in this manner so that the left and the right wall thickness can be metrologically captured at a point of the radiation. From this information and further information, the geometry can be exactly established or additionally controlled if, for example, a geometry value such as, e.g., the wall thickness is already known.

However, it is also conceivable that, in addition to the first radiation apparatus, a second or third radiation is arranged, in particular offset in height, within the device as described above. By means of the offset in height or, respectively, the different heights Hx of the detection region, the entire contour of the container can be established according to the method according to the invention via the (measured) height Hx. For this purpose, a large number of individual light points of the radiation sources of the radiation device can be arranged in a line on top of one another, which light points can be metrologically captured by line-shaped radiation sinks. It is also conceivable that the radiation apparatus is automatically adjustable in height, and therefore the offset in height can be generated in order to establish the geometry of the container via the height. In doing so, an individual measurement has to take place at each height Hx. However, if no line-shaped radiation source and radiation sink are used, simultaneous measurements of the geometry of the container take place via the height Hx.

It is also conceivable that another radiation apparatus or the first radiation apparatus is arranged in such a manner that the radiation emitted from the radiation source runs substantially parallel to the internal wall and/or the external wall in the lateral region or in the bottom region of the container. The radiation sink is primarily arranged such that it absorbs or receives in particular the radiation which has not been absorbed to the largest extent by the material of the wall.

Furthermore, within the context of the invention it is conceivable that the radiation apparatus is used at the same time as or at a time subsequent to the establishment of the geometry of the container for establishing a physical, chemical and/or biological property of the flowable medium. In doing so, a physical property, for example a density or the absorption and emission spectrum, a chemical property, for example the already depicted carbon dioxide concentration, and a biological property, for example a bacteria concentration, can be determined optically. Primarily after establishing the state of phase equilibrium between the individual media within the housing, a property or, respectively, a property value of the flowable medium and advantageously the carbon dioxide concentration of the medium is also established by means of the device according to the invention by using this radiation apparatus, which is also used for establishing the geometry. Thus, for example, the temperature of the flowable medium within the container can be captured by an infrared measurement. Furthermore, electromagnetic radiation from the radiation source can be emitted through a region of the container to a radiation sink of the radiation apparatus, which region is not filled with the flowable medium but with the gaseous medium, that is, preferably filled with carbon dioxide, so as to determine the carbon dioxide. Therefore, the radiation is in particular guided through a neck region and/or mouth region and/or head region of the container if the container is advantageously standing upright with the mouth region oriented upwards. When measuring or determining the property, a total pressure, that is, an absolute pressure at a defined temperature inside the container is primarily determined by use of the radiation apparatus, wherein the carbon dioxide concentration is represented as partial pressure of the gaseous medium. Here, the Henry law is used, which implies that the partial pressure of a gas or a gaseous medium above a liquid is directly proportional to the concentration of the gas in the liquid medium. It is conceivable that when determining the property, the container is rotated about its longitudinal axis at a defined and in particular constant speed v. Thus, it would be possible that the container is subjected to three measurements, wherein the container is rotated after each measurement by approx. 60° in one direction (left or right) about its longitudinal axis until, after three measurements, the container has been rotated by 180° about its longitudinal axis. Thus, the radiation apparatus used for establishing the geometry of the container is advantageously also used for establishing a property of the flowable medium in the container. This saves again an additional measuring apparatus which, in turn, results in space savings in the measurement laboratory and/or in the production line as well as in time and cost savings. In particular when establishing a property of the flowable medium by means of a radiation apparatus and in particular by means of a laser or an infrared radiation apparatus, it is necessary to know the internal geometry and/or the internal contour of the container so as to be able to exclude measurement errors of the property based on the container geometry or to be able to include the container geometry in the calculations of the property of the flowable medium.

Furthermore, it is therefore conceivable that the radiation source of the radiation apparatus emits infrared radiation at least indirectly to the radiation sink of the radiation apparatus, which infrared radiation is at least partially absorbed and/or reflected by a physical, chemical and/or biological property to be established of the flowable medium. In the present case, "indirectly" means that the radiation is emitted to an above-mentioned mirror or reflection apparatus which reflects the radiation or waves back to the radiation sink with almost no loss.

It is also possible that the wavelength of the emitted electromagnetic radiation is varied at least temporarily during establishing of the geometry of the container and/or establishing of the physical, chemical and/or biological property of the flowable medium. Therefore, the measuring accuracy can advantageously be increased.

Furthermore, claimed is a device according to the invention for establishing a geometry of a container for packaging a flowable medium, which device has at least one movement apparatus for rotating and/or swiveling the container about an axis of rotation, a radiation apparatus for generating and emitting at least electromagnetic radiation from a radiation source of the radiation unit to a radiation sink along a detection path, a detection apparatus for detecting a passage time of a container region through the detection region, and an evaluation apparatus for establishing at least an external geometry of the container based on the passage time.

Advantageously, the device for establishing the geometry is the same device which is used for establishing a physical, chemical and/or biological property of a flowable and in particular liquid medium that is introduced into the container. It is conceivable in this context to perform non-destructive testing of the sample product and in particular of the sample container. However, it is also conceivable that at least due to moving and/or agitating the container, carbon dioxide is released from the flowable medium to such an extent that a sufficient product quality and a minimum shelf life of the product or the flowable medium can no longer be ensured, so that the sample container is no longer available for further sale. It is also conceivable that prior to the process of establishing a property of the flowable medium and possibly also prior to the process of measuring or establishing a geometry of the container, in particular a closure element of the container is pinched by means of a tapping element or tapping mandrel in order to preferably release or extract the gaseous medium which is located above the liquid medium in the head space of the container and which is primarily an air-carbon dioxide mixture. The reason for doing this is, for example, that after the agitation process of the container, during which the container is moved or rotated or tilted, the head space or head region of the container, which now no longer contains air or gas, can be filled only with a gas, such as the carbon dioxide, that escapes from the liquid medium. This results in clear and advantageously in undistorted measurement results when establishing the carbon dioxide concentration in the liquid and/or flowable medium.

It is conceivable within the context of the invention that the device includes a calculation apparatus for calculating the internal geometry from a value of the external geometry and value of a wall thickness of the container. The calculation apparatus can be integrated in the device itself as a separate component part or can be a component part of the detection device or can be an externally arranged apparatus which is connected to the device at least for data transmission via cable or wireless via Bluetooth or wireless LAN. Advantageously, the device also includes a transmitter apparatus, a receiver apparatus or a combined transmitter and receiver apparatus, a storage apparatus, a display apparatus and/or an input apparatus. If the display apparatus is configured as a touchscreen, it can, at the same time, also serve as an input apparatus. For example, data concerning the medium within the container, which are in particular necessary for establishing the properties of this medium, can be input by means of the input apparatus. However, these values can also be input via a scanning unit of the device, at least indirectly via a corresponding code, such as a bar code, a QR code, a color code or a comparable code. The corresponding code can be arranged directly on the sample container or, respectively, container to be inspected or measured and/or can be placed on a large packaging or a bundle for packaging a batch of the product. Advantageously, the scanning unit is configured as external apparatus which belongs to the device and which is connected to the device in a wireless manner or via cable for data transmission.

Established and input values and data can be stored at least temporarily and preferably long-term in the storage unit. The transmitter and receiver unit advantageously serves for receiving data, for example about the container to be examined and/or the medium to be examined, from an external computer or server and, in turn, for transmitting data or values regarding the established geometry of the container and/or the established property of the medium to an external computer or server etc.

Furthermore, it is conceivable that the radiation source of the radiation apparatus is at the same the radiation sink so that both units of the radiation apparatus are arranged on one and the same side of the device. The radiation source emits an electromagnetic beam or, respectively, electromagnetic waves which are at least partially absorbed on a wall of the container and partially reflected back to the radiation source, which now is at the same time the radiation sink for receiving the radiation. The radiation which passes through the wall of the container and is partially refracted by the same then impinges on a reflection element, such as a mirror, which is arranged in the device opposite to the radiation source and radiation sink in the radiation path. This reflection element then reflects the radiation back again, wherein the radiation can travel again through the walls of the container.

Advantageously, it is possible that the radiation source of the radiation apparatus is a laser for emitting at least one laser beam and/or that the radiation sink of the radiation apparatus is a photodetector for receiving the laser beam. Furthermore, it is conceivable that not only one laser beam is emitted, but a plurality of laser beams are emitted from the radiation source, wherein the beams run substantially parallel to one another and advantageously span a three-dimensional space, but at least a two-dimensional plane, e.g. over the height.

Within the context of the invention, the radiation apparatus serves for establishing a geometry of the container and also, as already described above, for establishing a physical, chemical and/or biological property of the flowable medium, and in particular for establishing the carbon dioxide content of the medium. In the process of this, the movement apparatus, by means of which a region or portion of the container is moved through the detection region, advantageously also serves for implementing the agitation process of the container or, respectively, the mixing process of the media within the medium, namely the flowable medium and the gaseous medium.

Moreover, it is conceivable that the device includes an accommodation device for at least partially accommodating the container. This accommodation device can be configured in the form of an accommodation container or body in which the container is at least partially inserted. Accordingly, it is possible that the accommodation device is made from a transparent material such as, for example, a plastic material or at least has a transparent viewing window. In particular, an accommodation device comprising a plastic material can be produced cost-effectively, is low-maintenance and low in weight. The weight is in particular relevant with regard to an intended movement of the container for implementing a state of phase equilibrium of the media within the container. Thus, it is conceivable that a drive unit is arranged on the accommodation device itself in order to move or, respectively, rotate or agitate the accommodation device together with the container arranged therein. Furthermore, it is conceivable that the container together with an insert element is inserted into a region of the accommodation device. The insert element advantageously serves for arranging the container within the accommodation device and therefore within the device, and in particular for aligning it centrally, that is, centering it and advantageously adjusting or aligning it in height. Furthermore, it is conceivable that the accommodation device can be rotated or tilted not only about a defined axis of rotation or a defined center of rotation in order to move the container at least temporarily into an upside down position, wherein the axis of rotation advantageously extends perpendicular to a longitudinal axis of the upright standing container and thus also to a longitudinal axis of the accommodation device situated in a starting position. Rather, it is also possible that the accommodation device moves or rotates about an axis of rotation which extends substantially vertical and thus parallel to a longitudinal axis of the container (in the upright state). This makes it possible to rotate the container about its longitudinal axis, in particular during determining or establishing a property of the flowable medium.

The device advantageously serves for carrying out the above-described method.

All advantages that have already been described with respect to the method for establishing a geometry of a container for packaging a flowable medium apply also to the described device.

BRIEF DESCRIPTION OF THE SEVERAL VIEWS OF THE DRAWINGS

A device according to the invention is explained in greater detail below with reference to the drawings. In the figures, schematically.

DESCRIPTION OF SPECIFIC EMBODIMENTS OF THE INVENTION

Elements and technical features having the same function and mode of action in the FIGS. 1, 2, 3 and 4 are in each case designated by the same reference signs.

Figure 1:
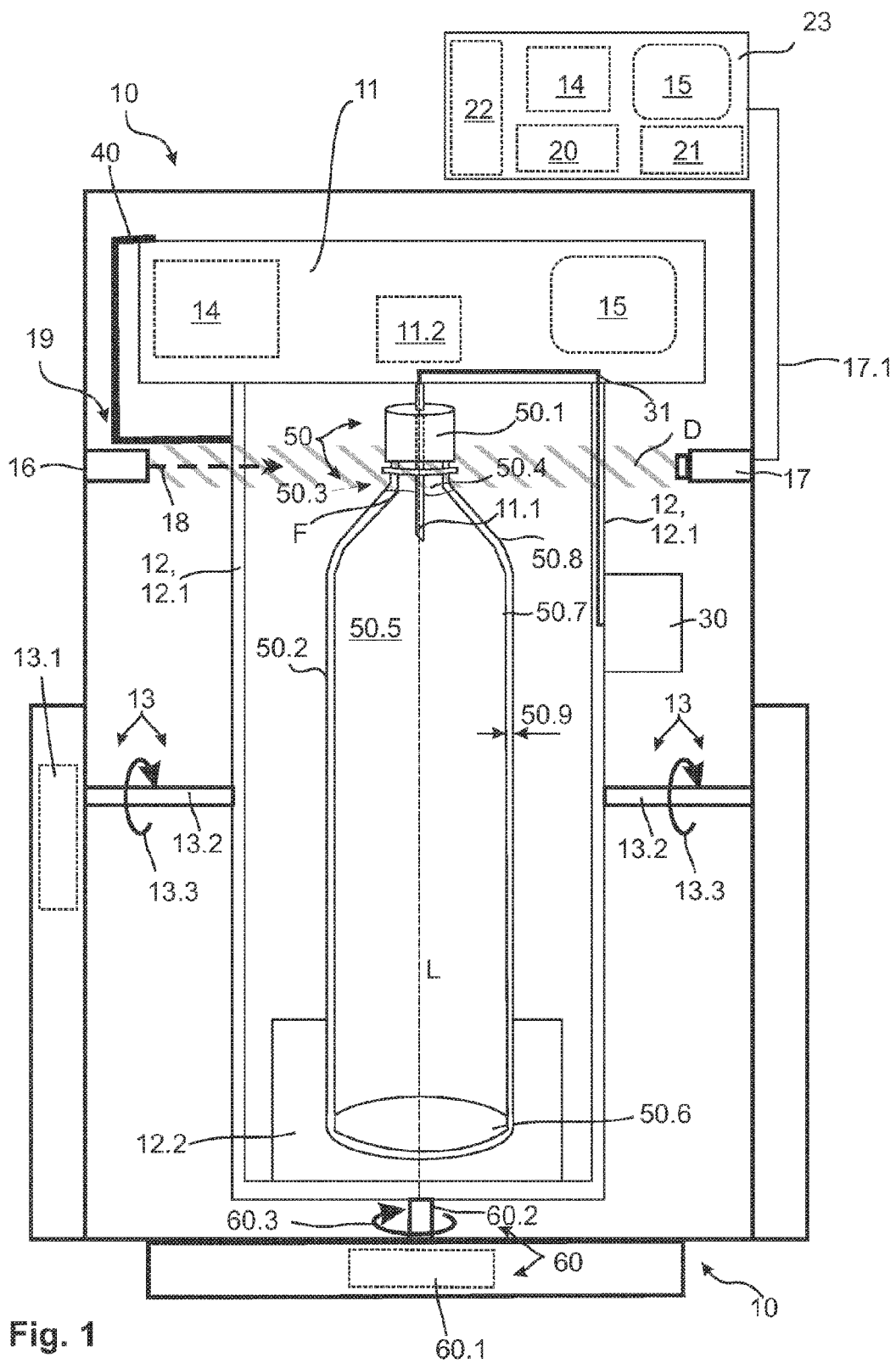
FIG. 1 shows a side view of a device for establishing a geometry of a container having a tapping mandrel.

FIG. 1 shows schematically a side view of a device 10 for establishing a geometry of a container 50 having a tapping mandrel 11.1. The container 50 is advantageously filled with a flowable medium 50.5, wherein filling in the medium is carried out at a filling station, for example. The liquid or flowable medium 50.5 introduced into the sealable container 50 is preferably (drinkable) food and preferably a beverage. The device 10 has a mechanical accommodation device 12 or, respectively, a mechanical accommodation container 12 for accommodating and arranging the container 50 on or in the device 10. The container 50 to be examined or, respectively, the container 50 containing the flowable medium 50.5 to be examined, is in particular a container for liquids in the form of a bottle which has a mouth region 50.3 or neck region 50.3 or a head space 50.3 as well as a body region 50.2 and a bottom region 50.6. Advantageously, one component part of the container 50 is the closure element 50.1 which, for example, is a screw cap, a crown cap or a cork stopper or a comparable cap. A fill level F of the liquid medium 50.5 in the container 50 is also indicated schematically. Advantageously, the container 50 is filled up to a neck region 50.3 or up into this neck region 50.3 with the liquid medium 50.5. Above the fill level F in the head space 50.3, which usually is not filled with the liquid medium 50.5, there is a gaseous medium 50.4 which usually contains carbon dioxide ($CO_2$). In order to prevent this gas 50.4 in the head space 50.3 from escaping, the container 50 or, respectively, the body region 50.2 of the container 50 is closed with the closure element 50.1.

Furthermore, as can be seen in FIG. 1, the container 50 is tapped by a tapping means 11.1 or tapping mandrel 11.1, and is pierced in particular in one region, primarily in the region of the closure element 50.1. The tapping mandrel 11.1 can protrude through a wall of the closure element 50.1 up into the liquid medium 50.5. However, within the context of the invention it is sufficient if the tapping mandrel 11.1 is fed or extends through the closure element 50.1 up into the head space 50.3 of the container 50 and therefore does not contact the liquid medium 50.5 when the container 50 stands upright on its container bottom 50.6. Advantageously, the tapping mandrel 11.1 itself is a component part of the measuring head apparatus 11 which, viewed in the vertical direction, is arranged above the closure element 50.1. The measuring head apparatus 11 can also serve for sealing the closure element 50.1 when tapping this closure 50.1 by means of the tapping mandrel 11.1, which, in the present case, is not shown in FIG. 1 for the sake of a better understand of the invention. In the measuring head apparatus 11, which can primarily be associated with the device 10 according to the invention as a component part, at least one measuring unit 11.2 and in particular a sensor 11.2 can be arranged. This measuring unit 11.2 can in particular be a temperature measuring unit or a temperature sensor. It is also possible that a plurality of measuring units 11.2 are provided in the measuring head apparatus 11, which can also directly and metrologically detect the properties of the liquid medium 50.5 and/or the gaseous medium 50.4 through the tapping mandrel 11.1.

Furthermore, the device 10 is equipped with a (first) movement apparatus 13 and in particular with a rotating and swiveling apparatus 13 or, respectively, a rotating and swiveling mechanism 13. Advantageously, the movement apparatus 13 includes a bracket-like element 12.1 or, respectively, a bracket 12.1 which serves either for securely accommodating the container 50 in the device 1 and to arrange this container on the movement apparatus 13, or to arrange the accommodation device 12, which can at least partially accommodate the container 50, on the movement apparatus 13 and to connect it thereto. At the lower distal end of the accommodation device 12, an insert element 12.2 can be arranged which, in addition to the centering and adjusting the height of the container 50 within the accommodation device 12 and therefore in the device 10, also serves for holding the container 50 in a form-locking or force-locking manner. Thus, the container 50 can advantageously be adjusted and/or arranged within the device 10 in a geometrically exact manner, that is, centered and adjusted in height, by means of the accommodation device 12 and in particular the insert element 12.2 thereof.

The measuring head apparatus 11, which is advantageously also connected via a clamping element 40 to the accommodation device 12 and in particular to the bracket 12.1 and therefore to the movement apparatus 13, can additionally have an evaluation apparatus 14 and a display unit 15. However, it is also conceivable that the measuring head apparatus 11 has a data transmission connection to a determination apparatus 30, wherein the determination apparatus 30, in addition to the evaluation unit 14 and the display unit 15, also has a storage unit 20 for storing input and/or established data and values, such as measured pressure values and/or temperature values, and a transmitter and receiver unit 21 for receiving measured values (pressure/temperature), for example from the measuring head apparatus 11 and for transmitting values that are input via a input unit 22, such as data about the type or composition of the flowable medium 50.5 to be examined, the type of container 50 (glass material, plastic material etc.). Moreover, it is also possible that the display unit 15 is a touch-sensitive screen (touchscreen) via which therefore data and/or values can be input so that the display unit 15 can at the same time also represent an input unit 22 and that a separate input unit 22 could be omitted. The data transmission between the measuring head apparatus 11 and the determination apparatus 30 can take place via a wired or wireless connection, for example via Bluetooth or wireless LAN. It is also conceivable that the determination apparatus 30 with the corresponding units 14, 15, 20, 21 and/or 22 is integrated in the measuring head apparatus 11 and therefore constitutes an integral part of the measuring head apparatus 11. Advantageously, the determination apparatus 30 is arranged stationarily on the device 10 and therefore, in contrast to the measuring head apparatus 11, does not move with the accommodation device 12 and the container 50 arranged therein about a defined center of rotation or a defined axis of rotation 13.2 at least temporarily in a defined direction of rotation 13.3.

Moreover, it is conceivable that the bracket 12.1 is not only arranged on an accommodation device 12, which is primarily configured as an at least partially closed housing having an input opening, in particular in the form of a cylinder, and that it surrounds this accommodation device 12 at least in some regions. Rather, the bracket 12.1 itself can serve as an accommodation means and therefore largely replace the accommodation device 12, so that the insert element 12.2 is advantageously arranged directly on the bracket 12.1 and in particular on the distal end thereof in order to position, adjust and center the container 50. Furthermore, it is conceivable that, for example, an above-described temperature control unit, which is not illustrated here, is arranged within the accommodation device 12, and which can serve for controlling the temperature of the flowable medium 50.5 in order to be able to accelerate the setting of a state of phase equilibrium within the container 50.

Furthermore, at least one radiation device 19 can be arranged within the device 10, in particular in the region of or, respectively, at the height of the head space 50.3 of the container 50. The radiation apparatus 19 advantageously has a radiation source 17, for example in the form of a laser, as well as a radiation sink 17, for example in the form of a detector, in particular a photodetector. From the radiation source 16, electromagnetic radiation 18 such as, for example, infrared radiation or electromagnetic waves, is emitted to the radiation sink 17, namely along a detection region D, through at least one region of the container 50 and in particular a head region 50.3 of the container 50.

The radiation source 16 is in particular aligned in such a manner that the emitted radiation 18 or, respectively, the emitted electromagnetic waves 18 impinge substantially perpendicular on a longitudinal axis L of the container 50. The radiation sink, which is arranged on a side of the container 50 opposite the radiation source 16 and which can also be designated as optical sensor 17, can detect the emitted radiation 18 by measurement. Also, a radiation sink 17 or an optical sensor, which measures a portion of a reflected radiation 18, can be provided on the radiation source 16 itself. By means of the provided radiation source as well as the radiation sink 17, a non-destructive sample measurement regarding a property of the flowable medium 50.5 and in particular a simple, cost-effective, rapid and reliable establishment of the geometry of the container 50 can be performed. Advantageously, the emitted radiation 18 is not limited to light visible to the human eye, so that radiations 18 of a different wavelength are also conceivable.

The reference sign 40 designates a schematically illustrated clamping element which extends from an outside of the accommodation device 12 up to a region of the measuring head apparatus 11 and therefore connects the measuring head apparatus 11 preferably fixedly to the accommodation device 12. Arranging and/or locking the measuring head apparatus 11 on an opening of the accommodation container 50 and/or an upper region of the container 50, in particular the mouth region 50.3 and preferably the region on which the closure element 50.1 is arranged, is advantageously made possible by means of the clamping element 40. Accordingly, the clamping element 40 advantageously serves for locking the measuring head apparatus 11 on the opening of the accommodation container 50 and therefore for clamping the container 50 in place in the accommodation device 12, that is, between the accommodation device 12 and the measuring head apparatus 11 itself.

In order to achieve a particularly optimal sample preparation and primarily the setting of a state of phase equilibrium within the container 50, the device 10 is provided with the already mentioned movement apparatus 13 or, respectively, the rotating and/or swiveling mechanism 13. The latter can be driven by an electromechanical drive 13.1 which, for example, can be implemented by an electric motor (e-motor). The rotating and/or swiveling mechanism 13 rotates the bracket 12.1 and/or the accommodation device 12 together with the container 50 fixed thereon or therein and with the measuring head apparatus 11 arranged on the accommodation device 12. It is also conceivable that at least one radiation source 16 and/or a radiation sink 17 are/is arranged on the accommodation device 12 and are/is not connected stationarily to the device 10, as illustrated exemplary in FIG. 1.

Furthermore, FIG. 1 shows a removal unit 30, which is also designated as "snift collector". The removal unit 30 is primarily arranged in a region of the accommodation device 12 and/or the bracket 21.1 and therefore can move together with these components or, respectively, co-rotate about the axis of rotation 19. However, it is also conceivable that the removal unit 30 is arranged stationarily within the device 10 and only connected to the accommodation device 12 or, respectively, the bracket 12.1 via corresponding connecting elements. In both embodiments, a conduction element 31 for conducting in particular a gaseous medium 50.4 from the removal unit 30 up to the tapping mandrel 11.1 which is pointed in particular at its distal end which extends up into the interior of the container 50. By means of the removal unit 30 it is now possible to discharge a gaseous medium 50.4 such as, for example air or an air-carbon dioxide mixture from the head space 50.3 of the container 50 via the tapping mandrel 11.1. In doing so, this gaseous mixture 50.4 can be fed to an externally arranged container (not shown here) or into the environment. Advantageously, the gaseous mixture 50.4 is removed before the beginning of the sample measurement and/or before the beginning of an establishment of the geometry of the container 50 and preferably also before the beginning of a movement of the container 50 for mixing the media and setting the state of phase equilibrium within the container 50 in order to preferably be able to extract in particular air contained in the container 50.

Furthermore, FIG. 1 shows a further (second) movement apparatus 60 which likewise can be driven via an electromechanical drive 60.1, such as an electric motor 60.1. Here, a shaft 60.2 is driven in a direction of rotation 60.3 in such a manner that in particular the bracket 12.1 and/or the accommodation device 12, which are/is also operatively connected to the second or, respectively, further movement apparatus 60, can be moved in the direction of rotation 60.2. Therefore, the container 50 rotates about its own longitudinal axis L which extends from the head region 50.3 up to the bottom region 50.6 of the container 50. Measuring the geometry of the container 50 at different measuring points as well as establishing the property of the flowable medium 50.5 by establishing the pressure of the gaseous medium 50.4 at different measuring points increases the measurement accuracy and decreases measuring errors, as a result of which more accurate and detailed measurement results can be provided.

By the reference sign 50.9, a wall thickness of the container 50 is illustrated, which wall thickness, for example, can be stored as a specified value in the storage unit 20 or can be established via another measuring apparatus such as another radiation apparatus which, however, is not shown here. According to the present invention, the geometry and in particular an external contour or external geometry 50.8 or an external geometry 50.8 of the container 50 is established based on the detected reflection, absorption and/or refraction of the radiation 18 on the container wall of the container 50, in addition to a physical, chemical and/or biological property of the flowable medium 50.5, by means of the radiation apparatus 19 and the radiation 18 emitted by the radiation apparatus 19. These values can then be transmitted to the calculation apparatus 23, for example via an transmission line 17.1, which can be configured in a wired or wireless manner. The calculation apparatus 23 is advantageously at the same time also the determination apparatus 23, which is used for determining a physical, chemical and/or biological property value of the flowable medium 50.5. From the value or data obtained for the external contour 50.8 and the value or data known or optionally determined for the wall thickness 50.9, the evaluation apparatus 14 of the calculation apparatus 23 can primarily calculate a value for the internal contour 50.7 or the internal geometry 50.7 or the inner geometry 50.7 of the container 50.

Figure 2:
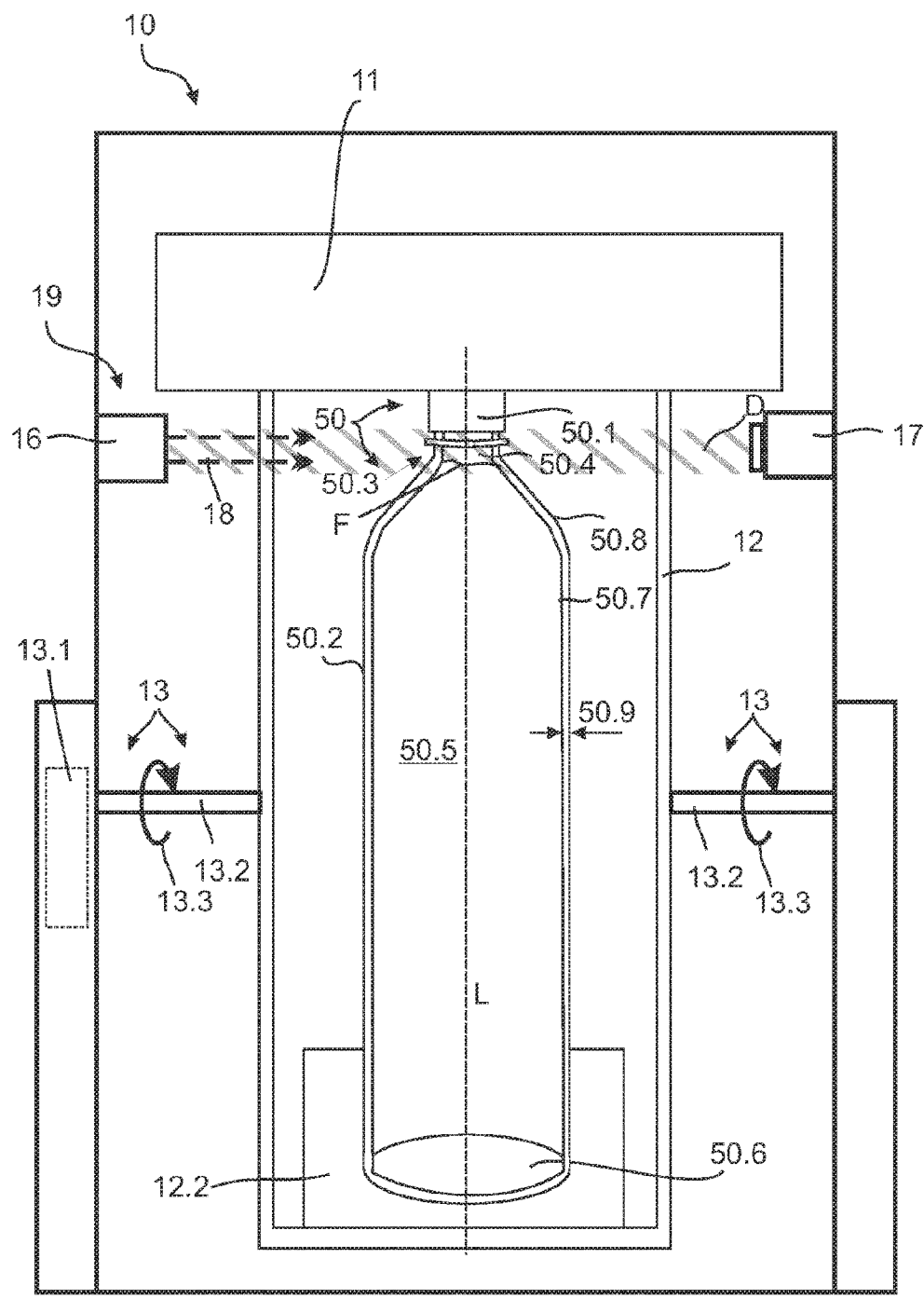
FIG. 2 shows a side view of a device for establishing a geometry of a container without a tapping mandrel.

FIG. 2 schematically shows a side view of a device 10 for establishing a geometry of a container 50 without a tapping mandrel. For a better understanding, FIG. 2 shows only individual components and elements and, respectively, apparatuses and units of the device 10 according to the invention as illustrated, for example, in FIG. 1. However, it is noted that all components shown in FIG. 1 can also be integrated in the device 10 according to FIG. 2. It is only intended to show that in contrast to the device 10 in FIG. 1, the device 10 can also be constructed without a tapping mandrel 11.1 (cf. FIG. 1). In this case too, it is conceivable that the measuring head apparatus 11 directly contacts at least the closure element 50.1 of the container 50, wherein the region of the closure element 50.1 can be accommodated by the measuring head apparatus 11 by means of locking elements, which are not shown here, in such a manner that during a rotational movement or agitating movement of the container 50 for sample preparation the container 50 cannot slip within the device 10.

Furthermore, FIG. 2 shows schematically that the radiation apparatus 19 and in particular the radiation source 16 thereof can also emit a plurality of radiations 18, wherein the radiations 18 advantageously run substantially parallel and spaced apart from one another through the detection region D. The radiation source 16 is preferably a line laser which can emit a plurality of line laser beams, then also called line laser, wherein therefore the radiation sink 17 is also configured as a kind of line sensor in order to be able to receive a plurality of radiations or, respectively, line laser beams.

Figure 3:
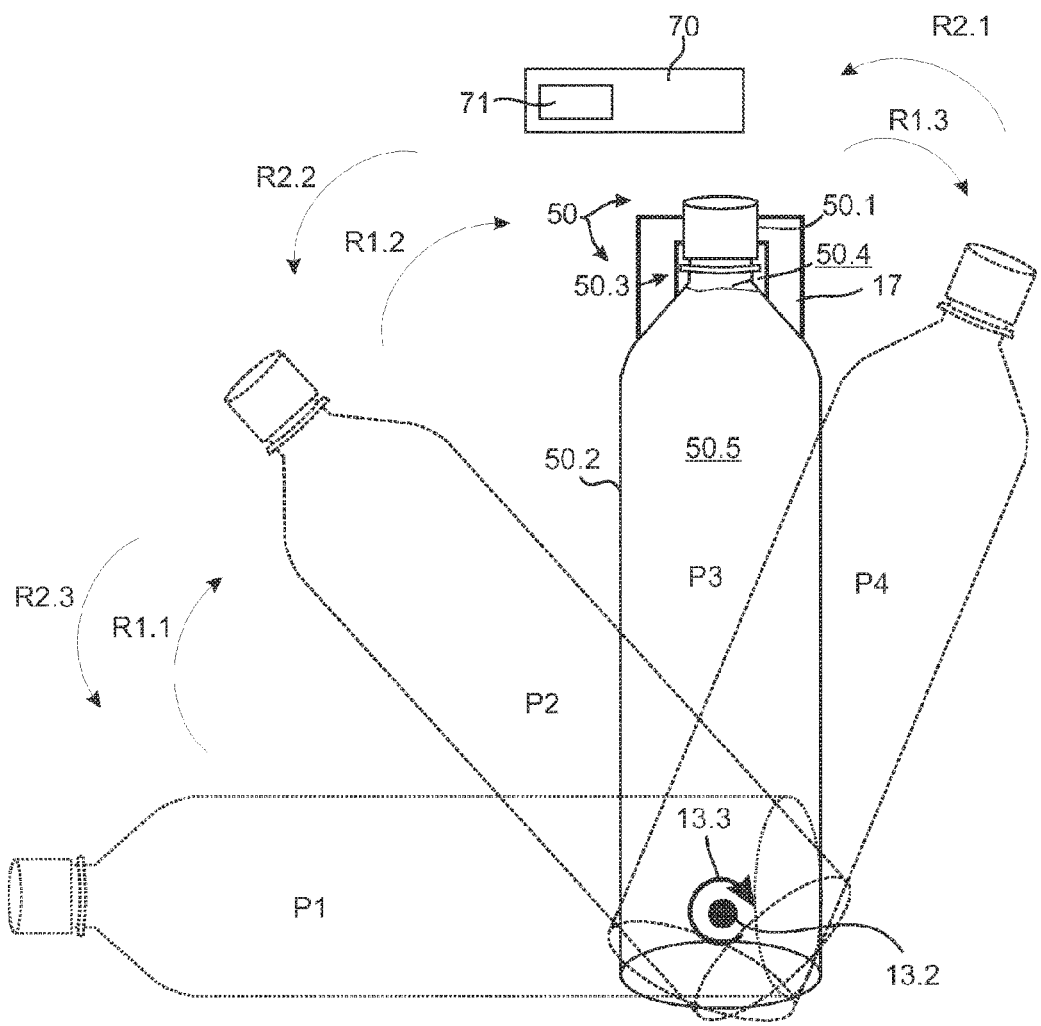
FIG. 3 shows a rotational movement of a container for establishing the geometry of the container within a device according to the invention.

FIG. 3 shows schematically a rotational movement of a container 50 for establishing the geometry of the container 50 within the device 10 according to the invention (cf. FIGS. 1 and 2). Here, the viewer therefore looks in the direction from the radiation source 16 (cf. FIG. 1 or FIG. 2), following the emitted beams 18 (cf. FIG. 1 or FIG. 2), at the radiation sink 17 and at the containers 50 or their container regions running through the detection region D (cf. FIG. 1 or 2). In order to be able to establish a property of the flowable medium 50.5, such as, for example, the carbon dioxide content thereof, it is necessary to appropriately prepare the sample prior to the measurement or, respectively, the establishment of the property. For this purpose, the container 50 filled with the flowable medium 50.5 and sealed with a closure element 50.1 is moved by means of the movement apparatus 13 shown in FIG. 1 or FIG. 2 about an axis of rotation 13.2 in a direction of rotation 13.2, whereby the liquid medium 50.5 in the container 50 moves in particular in such a manner that the carbon dioxide is released from the liquid medium 50.5. A movement of the container 50 advantageously takes place until a state of phase equilibrium is obtained. This movement about the axis of rotation 13.2 is also utilized for being able to establish a geometry and in particular an external geometry 50.8 of the container 50. The container 50 which is rotated about the axis of rotation 13.2, for example in a first direction of movement R1.1 and R1.2 and R1.3 from a first position P1 into a fourth position P4 passes or runs in the process of this through the detection region D (cf. FIG. 1 or 2). This means that during a movement in a first direction of movement R1.2 from position P2 or P1 to position P3, entering into the detection region can be detected and during a movement in a first direction R1.3 from position P3 to position P4, exiting the detection region can be detected by a corresponding detection apparatus 70, which can be connected, for example, to a radiation sink 17 in a wired or wireless manner. The detection apparatus 70 and in particular an evaluation unit 71 of the detection apparatus 70 measures the time that the container 50, in particular a head region 50.3 of the container 50 needs until this container region has passed through the detection region D at a defined speed of rotational movement. The evaluation unit 71 can also be the evaluation unit 14 of the determination apparatus 23 so that it is therefore conceivable that the detection apparatus 70 is also the determination apparatus 23, wherein an additional evaluation apparatus can advantageously be saved. This, in turn, saves costs. From the time value, the evaluation unit determines a value "x" for an external geometry or, respectively, an external geometry 50.8 of the container 50. The container 50 advantageously moves always in one direction of rotation, as illustrated with the arrows R1.1, R1.2 and R1.3. In doing so, the container 50 can be permanently rotated in a circle without the need of stopping the movement. However, it is also conceivable that the container is always swiveled by only 180° or less about its axis of rotation 13.2, and after reaching an end position, is moved again in a direction opposite the first direction, namely in a second direction, as shown in particular by the arrows R2.1, R2.2 and R2.3, for example from a position P4 to a position P2 or P1.

Figure 4:
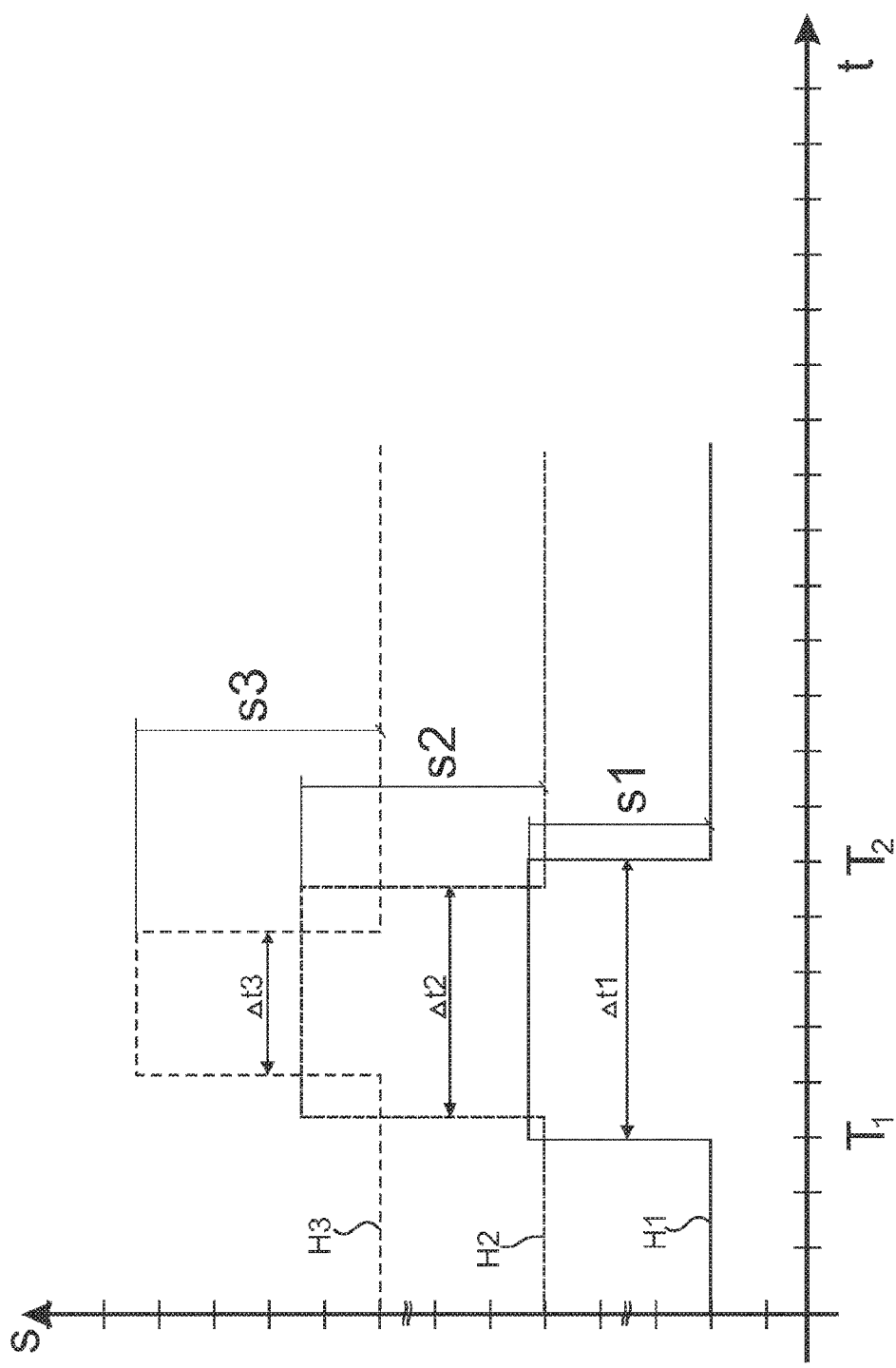
FIG. 4 shows an exemplary measurement diagram for establishing the geometry of a container according to the method according to the invention.

FIG. 4 schematically illustrates a measurement diagram of the method according to the invention. The time t is plotted on the x-axis, and the measurement signal s or, respectively, the exemplary change of the measurement signal s from the radiation apparatus 19, in particular the radiation sink 17, is plotted on the y-axis. For better clarification of the method, three different measurement signals s1 to s3 from the detection region are illustrated in a diagram at the respective heights H1 to H3.

First, only the signal curve at the height H1, which is shown as a solid line, is explained. The container 50 is slowly moved at a constant speed v at the height H1 to the detection region. At the time T1, the container enters the detection region, wherein a clear signal change s1 occurs, and this time T1 is stored. As long as the container 50 continues to move at the constant speed v (at the height H1) in the detection region, no significant signal change occurs during this measurement. A clear signal change s1 occurs again at the time T2 only when the container 50 exits the detection region (at the height H1). This time T2 is recorded and stored as well. From the difference between the two times T1 and T2, the time period or, respectively, the time Δt can be determined. Since the movement speed v of the container 50 is also known, it is now also possible through the product L=v*t to exactly determine the container's 50 length L upon entering the detection region, which corresponds to the external geometry or, respectively, the outer diameter L of the container 50 at the height H1. Thus, the desired measurement result is obtained.

The above-described measurement can be repeated at a different height H2 or H3 in the detection region, wherein the exemplary signal curves s2 and s3 in the diagram are indicated one above the other in dashed lines. The result of these comparable curves of the first measurement s1 is that the outer diameter L of the container 50 decreases across the heights H1 to H3 and therefore becomes narrower since the respective entering duration Δt1 to Δt3 noticeably shortens at a constant speed v.

As already mentioned, the measurement s1 to s3 can also take place simultaneously using a line-shaped radiation apparatus 19 or three point measurements one above the other at the heights H1 to H3.

REFERENCE LIST 10 device
11 measuring head apparatus
11.1 tapping mandrel
11.2 measuring unit/temperature measuring unit
12 accommodation device
12.1 bracket
12.2 insert element
13 movement apparatus/rotating and swiveling movement apparatus, -mechanism
13.1 drive
13.2 axis of rotation/rotating shaft
13.3 direction of rotation
14 evaluation unit
15 display unit
16 radiation source
17 radiation sink
17.1 transmission element
18 radiation/waves
19 radiation apparatus
20 storage unit
21 transmitter and/or receiver unit
22 input unit
23 determination apparatus/calculation apparatus
40 clamping element
50 container
50.1 closure element
50.2 body region
50.3 neck region/head space
50.4 gaseous medium
50.5 liquid medium
50.6 bottom region
50.7 internal geometry/inner geometry/internal contour
50.8 external geometry/outer geometry/external contour
50.9 wall thickness
60 further movement apparatus
60.1 drive
60.2 axis of rotation/rotating shaft
60.3 direction of rotation
70 detection apparatus
71 evaluation unit
D detection region
L longitudinal axis of the container
P1 position 1 of the container 50
P2 position 2 of the container 50
P3 position 3 of the container 50
P4 position 4 of the container 50
R1.1 first direction of movement from position P1 to P2
R1.2 first direction of movement from position P2 to P3
R1.3 first direction of movement from position P3 to P4
R2.1 second direction of movement from position P4 to P3
R2.2 second direction of movement from position P3 to P2
R2.3 second direction of movement from position P2 to P1

What is claimed is:

1. A method for establishing a geometry of a container for packaging a liquid medium, including the steps:
activating a radiation source for generating and emitting at least electromagnetic radiation to a radiation sink along gaseous medium in a detection region in a head space of the container which is filled up with the liquid medium up to the head space, at least rotating or swiveling the container about an axis of rotation, wherein at least from time to time during a rotational movement of the container, at least one container region is moved through at least one portion of the detection region, detecting a passage time of the container region through the detection region, and establishing an external geometry at least from the passage time.

2. The method according to claim 1, wherein at least an internal geometry of the container is established from a value of the external geometry and a value of a wall thickness of the container.

3. The method according to claim 1, wherein at least a value of the wall thickness of the container is established at least by means of a radiation apparatus comprising the radiation source or by means of a further radiation apparatus.

4. The method according to claim 1, wherein a radiation apparatus comprising the radiation source is used at the same time as or at a time subsequent to the establishment of the geometry of the container for establishing at least a physical, chemical or biological property of the liquid medium.

5. The method according to claim 1, wherein the radiation source emits infrared radiation at least indirectly to the radiation sink, which infrared radiation is at least partially absorbed or reflected or scattered by at least a physical, chemical or biological property to be established of the liquid medium.

6. The method according to claim 1, wherein a wavelength of the emitted electromagnetic radiation is varied at least temporarily at least during the establishing of the geometry of the container or the establishing of at least the physical, chemical or biological property of the liquid medium.

7. The method according to claim 1, wherein the external geometry is established by calculating the internal geometry from a value of the external geometry and a value of a wall thickness of the container.

8. The method according to claim 1, further comprising optically measuring at least a physical, chemical or biological property of the medium.

9. A device for establishing a geometry of a container for packaging a liquid medium, comprising
an accommodation device adapted for at least partially accommodating the container in a form-locking or force-locking manner;
a movement apparatus for at least rotating or swiveling the container about an axis of rotation,
a radiation source for generating and emitting at least electromagnetic radiation;
a radiation sink along gaseous medium in a detection region in a head space of the container which is filled up with the liquid medium up to the head space, and
an evaluation apparatus for establishing an external geometry of the container based on a passage time of a container region through the detection region;
wherein said radiation sink and said radiation source are mounted on said accommodation device such that the at least electromagnetic radiation impinges the head space of the container.

10. The device according to claim 9, wherein the at least electromagnetic radiation is emitted from the radiation source and reflected back through the detection region up to the radiation sink the radiation sink.

11. The device according to claim 9, wherein at least the radiation source is a laser for emitting at least one laser beam, or that the radiation sink is a photodetector for receiving the laser beam.

12. The device according to claim 9, wherein the radiation source serves for establishing at least a physical, chemical or biological property of the liquid medium.

13. The device according to claim 9, wherein the device serves for carrying out at least the method for establishing a geometry of the container for packaging the liquid medium, including the steps:
activating the radiation source and the radiation sink,
at least rotating or swiveling the container about an axis of rotation by means of the movement apparatus, wherein at least from time to time during a rotational movement of the container, at least one container region is moved through at least one portion of the detection region,
detecting the passage time of the container region through the detection region, and
establishing the external geometry at least from the passage time.

14. A method for establishing a geometry of a container for packaging a liquid medium, including the steps:
activating a radiation source for generating and emitting at least electromagnetic radiation to a radiation sink along gaseous medium in a detection region,
at least rotating or swiveling the container about an axis of rotation, wherein at least from time to time during a rotational movement of the container, at least one container region is moved through at least one portion of the detection region,
detecting a passage time of the container region through the detection region, and
establishing an external geometry at least from the passage time;
wherein a wavelength of the emitted electromagnetic radiation is varied at least temporarily at least during the establishing of the geometry of the container or the establishing of at least the physical, chemical or biological property of the liquid medium.

* * * * *